(12) United States Patent  
Lach

(10) Patent No.: US 6,673,096 B2
(45) Date of Patent: Jan. 6, 2004

(54) SYSTEM AND METHOD FOR TISSUE TREATMENT

(75) Inventor: Elliot Lach, Framingham, MA (US)

(73) Assignee: Biocellulase, Inc., Woburn, MA (US)

( * ) Notice: Subject to any disclaimer, the term of this patent is extended or adjusted under 35 U.S.C. 154(b) by 53 days.

(21) Appl. No.: 10/000,459

(22) Filed: Nov. 2, 2001

(65) Prior Publication Data

US 2002/0111656 A1 Aug. 15, 2002

Related U.S. Application Data

(60) Provisional application No. 60/245,948, filed on Nov. 3, 2000.

(51) Int. Cl.$^7$ .............................................. A61N 5/067
(52) U.S. Cl. ........................................... 607/89; 601/15
(58) Field of Search .......................... 607/88.89; 601/15

(56) References Cited

U.S. PATENT DOCUMENTS

| | | | | |
|---|---|---|---|---|
| 5,176,130 A | * | 1/1993 | Kim | 601/15 |
| 5,336,159 A | * | 8/1994 | Cheng | 601/15 |
| 5,464,436 A | * | 11/1995 | Smith | 607/89 |
| 5,587,396 A | * | 12/1996 | Smith | 514/557 |
| 6,090,101 A | * | 7/2000 | Quon et al. | 606/9 |
| 6,149,611 A | * | 11/2000 | Chen | 601/22 |
| 6,193,678 B1 | * | 2/2001 | Brannon | 601/15 |
| 2002/0193831 A1 | * | 12/2002 | Smith | 607/2 |

FOREIGN PATENT DOCUMENTS

DE    3941689 A  *  6/1991   ............. A61F/7/00

* cited by examiner

*Primary Examiner*—Michael Peffley
*Assistant Examiner*—Henry M. Johnson
(74) *Attorney, Agent, or Firm*—Lahive & Cockfield, LLP

(57) ABSTRACT

A system and method for the treatment of body tissue is provided that includes a radiation-emitting device and a massaging mechanism. In accordance with one embodiment, the radiation-emitting device is a laser and the massaging mechanism is an automated mechanical massaging mechanism. The radiation-emitting device can emit radiation in the visible and infrared wavelengths. The radiation-emitting device can emit radiation in a concentric combination of infrared and visible laser light. The method of using the tissue treatment system includes exposing a skin surface of a patient to radiation emitted from the radiation-emitting device at predetermined wavelengths for predetermined periods of time. The method further provides for massaging the exposed skin surface of the patient with the massaging mechanism. The tissue treatment system can be utilized to effect the reduction of excess cellulite.

19 Claims, 3 Drawing Sheets

SYSTEM AND METHOD FOR TISSUE TREATMENT

RELATED APPLICATION

This application claims priority to co-pending U.S. Provisional Application No. 60/245,948, filed Nov. 3, 2000, for all subject matter common to both applications. The disclosure of said provisional application is hereby incorporated by reference in its entirety.

FIELD OF THE INVENTION

The invention relates to treatment of a physical condition, and more particularly relates to a system and corresponding method of use for the treatment of body tissue, including reducing cellulite.

BACKGROUND OF THE INVENTION

Cellulite is not only prevalent in the overweight. It is estimated that between 90% and 98% of the total female adult population have had, will have, or currently do have, a desire to reduce an amount of cellulite. The male population also struggles with its desire to reduce cellulite amounts.

Once cellulite begins, it is chronic and spontaneously irreversible (without specific treatment). If extracted and chemically analyzed, cellulite is a jelly-like substance composed of water and fat. Cellulite becomes trapped in tissues. Unlike ordinary fat, cellulite is not readily available to the organism. Because it is trapped, it is relatively isolated from the natural processes of absorption and elimination.

Secondarily, cellulite interferes with circulation. The formation of cellulite partially occurs due to venous and lymphatic stagnation. The vicious cycle is then closed and tends to perpetuate itself.

Cellulite is a generalized condition that is fundamentally based on nutrition. As fat cells increase in volume and infiltration, they add to an already existing circulatory disturbance. This leads to a decrease in the local metabolic rate, which helps perpetuate the cellulite cycle. The sticky, fatty masses find locations in the connective tissue (otherwise known as interstitial tissue) between the skin and muscle in the subcutaneous layer. When there is a disturbance in the connective tissue, additional problems result. The additional problems occur in part because the connective tissue envelops all internal organs including the lymphatic system, which contributes to the pathway of all nutrients and wastes to and from the cells.

Increases of cellulite deposits literally waterlog the connective tissue, which eventually breaks down. The connective tissue then attempts to repair itself, eventually forming a fibrous scar tissue. The newly thickened tissue then traps more fat and water, which again develops cellulite.

A number of non-invasive methods currently exist that attempt to reduce cellulite on a temporary basis. These methods primarily involve the application of topical agents to reduce the appearance of cellulite on the thigh, which have been reported to be effective as a temporary means of cellulite reduction. Other methods of cellulite reduction involve targeted surgical adipose tissue resection in the fatty layers of the subcutaneous tissue. This method is considered an invasive procedure with potential risks and complications including pain, numbness, surface contour irregularity, and death. Other non-surgical but invasive means of cellulite reduction currently being investigated include methods of fat reduction by direct injection of antibodies to native fat, or injection of agents that otherwise accelerate resorption of fat.

SUMMARY OF THE INVENTION

There is a need for a tissue treatment system that treats body tissue, including effectively and efficiently reducing the occurrence and existence of cellulite in a patient. The present invention is directed toward further solutions to address this need. A tissue treatment system is provided that includes a radiation-emitting device and a massaging mechanism. In accordance with one embodiment, the radiation-emitting device is a laser and the massaging mechanism is an automated mechanical massaging mechanism.

The radiation-emitting device can emit radiation in the visible (e.g., light) and infrared wavelengths. In one example embodiment, the radiation-emitting device emits radiation in a concentric combination of infrared and visible laser light.

The teachings of the present invention further include a method of using the tissue treatment system having a radiation-emitting device and a massaging mechanism. The method includes exposing a skin surface of a patient to radiation emitted from the radiation-emitting device at predetermined wavelengths for predetermined periods of time. The radiation can be applied continuously or intermittently according to a preferred regimen. The method further provides for massaging the exposed skin surface of the patient with the massaging mechanism.

An additional step of calculating the predetermined wavelengths and the predetermined periods of time based at least partially on a measurement of cellulite in an area of the skin surface being treated is also provided.

The step of exposing the skin surface can include exposing the skin surface to laser induced radiation. The laser radiation can apply a concentric combination of infrared and visible laser light to the skin surface.

The method can further include the step of exposing the skin surface to an application of infrared radiation after exposure to the laser radiation. The application of infrared radiation can occur in a continuous wave. The application of infrared radiation can also occur at predetermined locations on the exposed skin corresponding to lymphatic drainage meridians.

The step of massaging the exposed skin surface can utilize a mechanical massage mechanism. The step of massaging the exposed skin can be executed by massaging from points distal from a heart of the patient to points proximal to the heart of the patient to encourage fluid flow toward the heart. Further, the step of massaging the exposed skin can include massaging in predetermined patterns of motion.

The tissue treatment system, and corresponding method of use, can be effective in treating a selected condition, such as unwanted tissue, edema, overactive sweat glands, cysts, lipomas, psoriatic tissue, acne, excess lymphatic fluid and tissue, varicose veins, telengiectasias, pain, inflammation, inflammatory products, and body toxins.

BRIEF DESCRIPTION OF THE DRAWINGS

The aforementioned features and advantages, and other features and aspects of the present invention, will become better understood with regard to the following description and accompanying drawings, wherein.

DETAILED DESCRIPTION OF THE INVENTION

The present invention generally relates to treating a selected patient condition, and preferably relates to tissue treatment. A tissue treatment system of the present invention applies laser radiation to an area targeted for, e.g., cellulite reduction, in a predetermined wavelength, or combination of wavelengths, intervals, periods, and patterns. The application of infrared radiation can optionally follow. Subsequent to the application of infrared radiation, the tissue treatment system massages the area targeted for cellulite reduction using a predetermined combination of massage techniques. Cellulite reduction results from the combined laser and massage applications. Other tissue treatments are possible with variation of the laser and massage applications. The new regimen can be determined by the ordinarily skilled artisan in light of the teachings herein.

Figure 1:
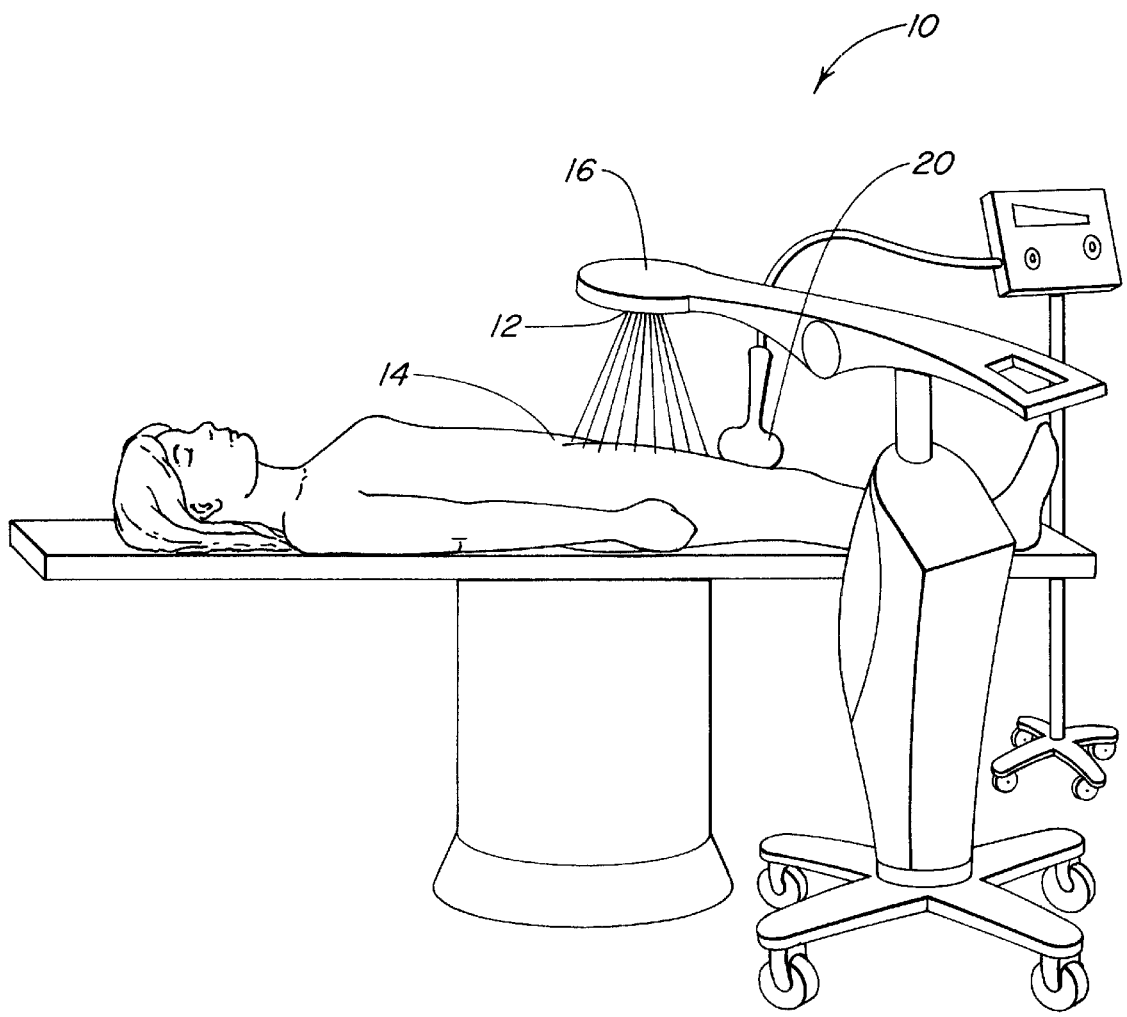
FIG. 1 is a diagrammatic illustration of a tissue treatment system according to one embodiment of the present invention.
Figure 2:
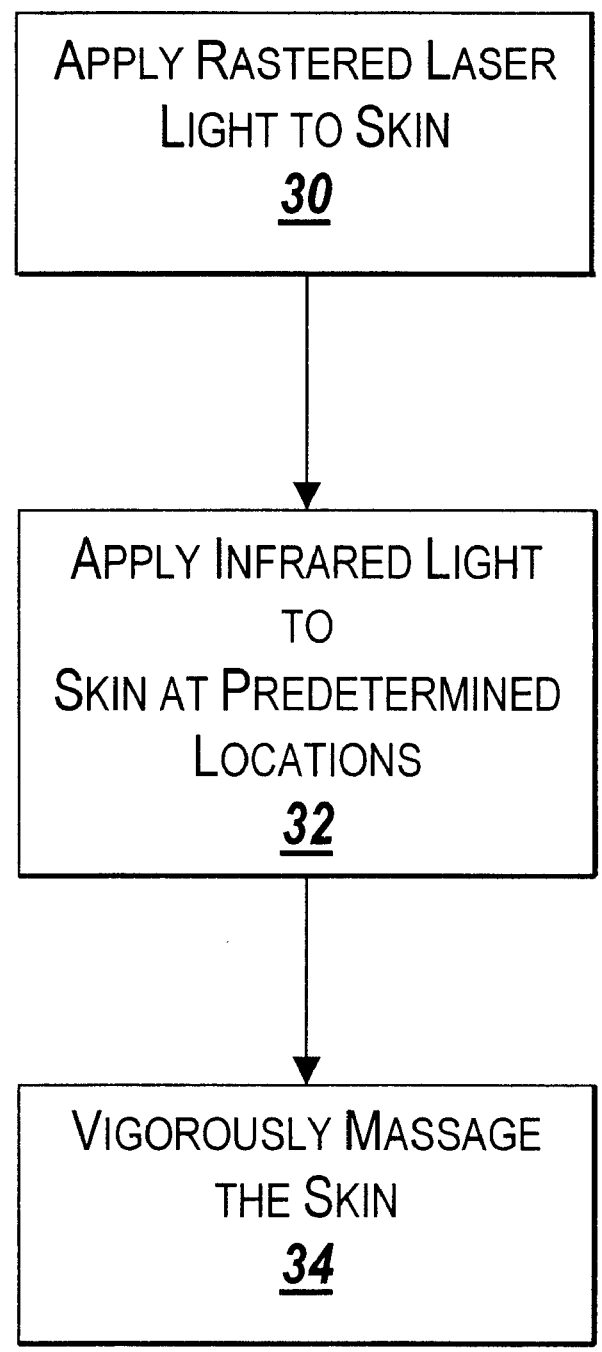
FIG. 2 is a flowchart illustrating a corresponding method of use of the system of FIG. 1.
Figure 3:
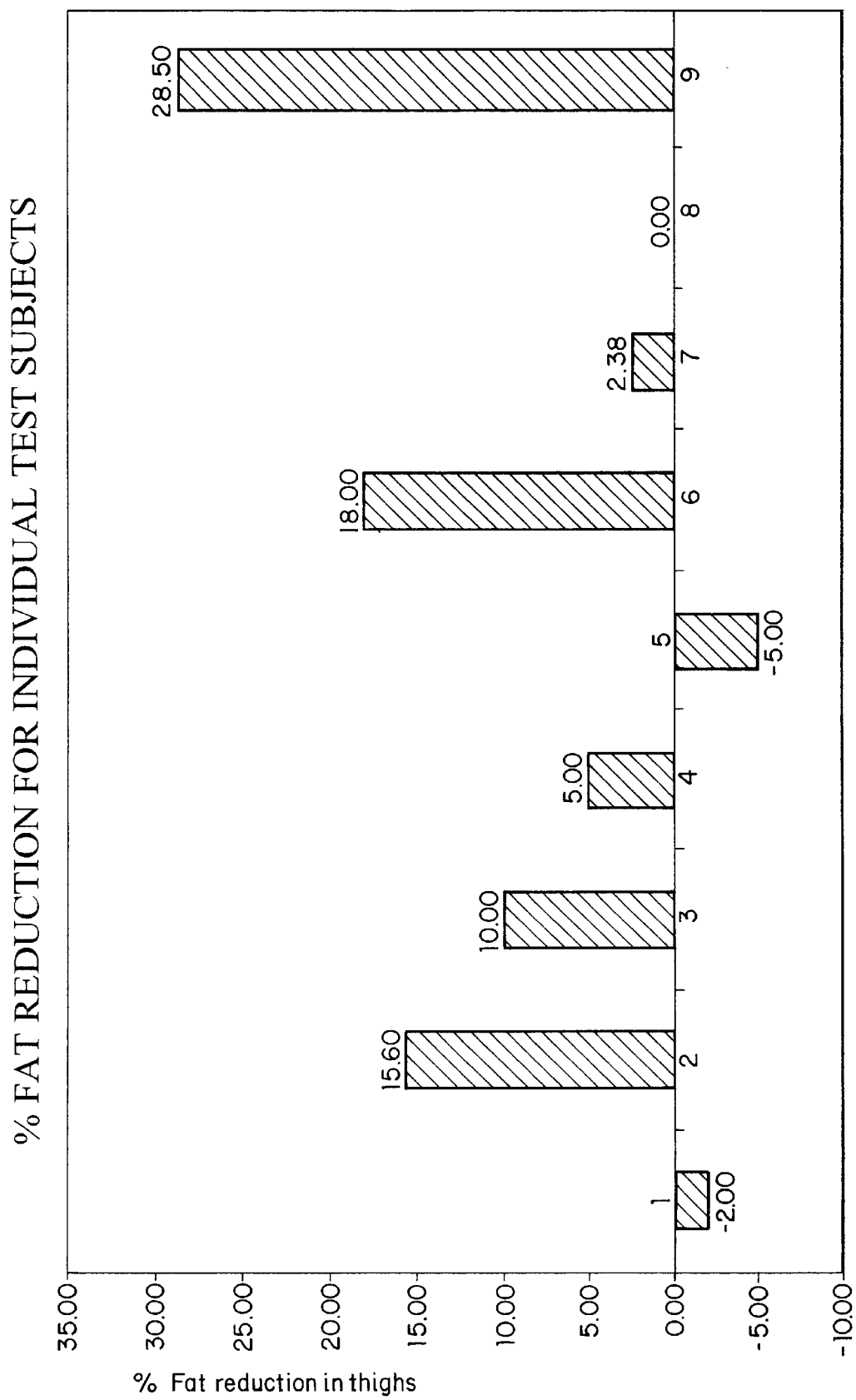
FIG. 3 is a graph plotting results of patients treated according to the teachings of the present invention.

Referring now in detail to the drawings wherein like parts are designated by like reference numerals throughout, FIGS. 1 through 3 illustrate a system and corresponding method for the treatment of a condition, and preferably a tissue, using the reduction of cellulite as an example embodiment, according to the present invention. Although the present invention will be described with reference to the example embodiments illustrated in the figures, it should be understood that the present invention can be embodied in many alternative forms. In addition, any suitable size, shape, or type of elements or materials can be utilized, and can be employed to treat the various conditions set forth above. For purposes of simplicity, we describe below treating tissue to reduce cellulite. This is not to be construed in a limiting sense.

Cellulite represents the excessive accumulation of fat cells within areas of connective tissue (in the subcutaneous layer) whereby additional microcirculatory and biochemical changes have taken place. This localized form of fat tends to affect the thighs, the medial side of the knees, the buttocks, and the medial and outer sides of the arms, the nape, abdomen, flank, and the ankles. In cellulite states, the fundamental substance of the connective tissue increases its degree of fluid retention and viscosity therefore resulting in poor capillary exchange, which interferes with the mobilization of the excess deposits of fatty tissue.

According to one aspect of the present invention a condition or tissue treatment system 10 is provided. The tissue treatment system 10, through a process of transcutaneous laser stimulation combined with infrared radiation treatment and subsequent skin massage, has many different effects. For the purpose of illustrating the tissue treatment system 10, the example effect of cellulite reduction will be described herein. However, it should be noted that the teachings of the present invention can be applied to a plurality of tissue treatments, as characterized below. For the instance of cellulite reduction, the application of infrared radiation and skin massage reduces the thickness of fat located in a subcutaneous location of a patient.

Turning first to FIG. 1, the tissue treatment system 10 is diagrammatically illustrated. The tissue treatment system 10 includes a radiation-emitting device, which can be in the form of a laser 12. The laser 12 is adapted to emit radiation at one or more wavelengths or wavelength ranges, and preferably emits differing wavelengths of radiation. The laser 12 mounts to any suitable support, such as a mechanical robotic scanner 16, which controls the application of the radiation to a skin surface 14 of a patient. The laser can emit radiation in the infrared wavelengths. Although not illustrated, the scanner 16 and/or the laser 12 can be coupled to a controller or data processing device for controlling the power and emitting sequence of the laser.

The controller or data processing device can be a programmable or programmed device that responds to a specific set of instructions in a well-defined manner and can execute a set of instructions. The device can include one or more of a storage device, which enables the computing apparatus to store, at least temporarily, data, information, and programs (e.g., RAM or ROM); a mass storage device for substantially permanently storing data, information, and programs (e.g., disk drive or tape drive); an input device through which data and instructions enter the computing apparatus (e.g., keyboard, mouse, or stylus); an output device to display or produce results of computing actions (e.g., display screen, printer, or infrared, serial, or digital port); and a central processing unit including a processor for executing the specific set of instructions.

The tissue treatment system 10 further includes a mechanical massaging mechanism 20 for use in conjunction with the laser 12. The mechanical massaging mechanism 20 can apply different massage techniques to the patient. By mechanical massaging mechanism 20 what is meant is any suitable device for applying mechanical or electrical physical stimulus to an area of a patient's skin or body tissue. For example, the mechanical massaging mechanism 20 can include one or more spherical components, rolling components, kneading components, vibrating components, and the like. The mechanical massaging mechanism 20 can execute different massage techniques as known to those of ordinary skill in the art, and have any selected shape or take any selected form.

The operation of the tissue treatment system 10 according to one aspect of the present invention is illustrated in FIG. 2. The laser 12 can, if directed, emit radiation at particular wavelengths. The laser 12 is rastered across the skin surface 14 utilizing the mechanical robotic scanner 16 in a continuously-on laser mode (step 30). The mechanical robotic scanner 16 positions the laser 12 approximately eighteen inches from the skin surface 14. Those of ordinary skill in the art will readily recognize that the laser 12 utilized in this embodiment focuses at the approximate distance of eighteen inches from the skin surface 14. However, this distance can be varied to apply different intensities of radiation. Those of ordinary skill in the art will recognize that different laser configurations and operational modes can be employed. Further, the laser 12 utilized in the described embodiment is a fixed power laser, such that the power only varies with the exposure time; i.e., increase exposure time to increase the power. One of ordinary skill in the art will appreciate that other laser configurations having variable power outputs, or different power levels, can be employed in accordance with the teachings of the present invention.

The tissue treatment system 10 applies at least two different laser 12 wavelengths to the patient during the course of the application. The radiation can be emitted at different wavelengths, at different intervals, and for different time durations. First, the laser 12 projects radiation having wavelengths in a concentric combination of infrared and visible laser light, for example between about 650 nanometers and about 1295 nanometers.

The duration, power, and wavelengths of the application of the laser 12 depends primarily on a formulation of different factors, such as calf circumference, thigh circumference, abdominal circumference, hip circumference, patient weight, and patient height. For example, a patient having a thigh circumference of 38 cm, calf circumference of 31 cm, abdominal circumference of 76 cm, hip circumference of 82 cm, weight of 62 kg, ideal body weight of 50 kg according to Standard Metropolitan Life Insurance Company Tables, and height of 5 feet 3 inches, would be exposed to the rastered radiation for 6.4 minutes per area. The time duration for exposure of each area on the skin surface 14 is calculated based on the following expression: (Hip Circumference in cm)/(Abdominal Circumference in cm)×(Weight in kgs)/(Ideal Body Weight in kgs)×(Calf Circumference in cm+Thigh Circumference in cm)×Reduction Factor=Time in Minutes. Ideal Body Weight ("IBW") is as defined by Standard Metropolitan Life Insurance Company tables for IBW calculated from the patient's height. The Reduction Factor is 0.07 with a minimum exposure of 5.5 minutes per area. The maximum exposure per area for a majority of the patients is about 12 minutes. However, this number may vary depending on the above variables. Again, the power of the laser 12 in the described embodiment is fixed. However, a laser having variable power settings can be employed, and the above relationship of variables adjusted for different power settings.

The typical exposure time per area being exposed is between about five and twelve minutes for an individual female adult of average build. For example, the thigh area can be treated in three sections, each area encompassing 120 degrees of the thigh with approximately 20% overlap. Thus, for each thigh, the laser treatment time is approximately three times the duration of exposure for each area, or eighteen to thirty minutes per limb. The duration of exposure varies depending on the actual values of the above-mentioned variables. The laser 12 is delivered as a continuous wave beam rastered across the skin surface 14. The entire skin area to be treated may be covered by a single scan at a rate of about 1 Hz.

Upon completion of the laser scan session, an infrared radiation emission is then administered to the skin surface 14 at sixteen discrete sites along each single thigh (step 32). The sites are at approximately the lymphatic drainage meridians known to those of ordinary skill in the art. Each site is exposed for a period of approximately 30 seconds. The sites correspond to different lymphatic drainage points, and are different for different parts of the body. Further, the infrared radiation can be applied in a number of different patterns, such as oval, square, circle, etc., to most efficiently cover a target area as required. A more typical application involves a generally circular motion, with a final whisking in the general direction of the heart.

The laser treatment heats deep tissue within the body of the patient at the targeted locations exposed to the laser 12. The deep heating of the laser 12 can also be delivered to deep muscle, tendon, fascia, and bone structures within the body of the patient. Concentrated delivery of heat into the fat layer can cause the desired lipolysis, which is the hydrolysis of lipids, i.e., the decomposition of the organic compounds forming the cellulite.

Following the application of the laser 12 in the different wavelength combinations, the mechanical massaging mechanism 20 applies a vigorous massage to the portions of the skin surface 14 that were treated with the laser and infrared wavelengths (step 34). As an example embodiment, a massaging machine made by Spade-Soleil formed the massage portion of the tissue treatment system 10 and was utilized to execute the massage. The mechanical massaging mechanism 20 applies a number of predetermined different massage patterns and techniques to the areas targeted for cellulite reduction. In the example of a thigh, each side of the thigh is massaged for approximately 4 to 6 minutes, however, the duration of the massage can vary to the extent required for optimal cellulite reduction as specified by the particular circumstances surrounding the patient. The massaging motion occurs from a point distal from the heart to points proximal to the heart to encourage fluid flow toward the heart.

Fat is a component of cellulite. Therefore, reduction of fat by the laser application reduces the appearance of cellulite. However, if an individual does not maintain an appreciable level of cellulite, that reduction and ablation of fat results in other benefits, such as reduction of blood pressure, and reduced insulin requirements. A visible reduction in cellulite may not occur in such an instance, because the cellulite was not visible prior to treatment.

In a further example embodiment, an experimental application was executed, the results of which are plotted in FIG. 3. The graph shows the percentage of fat reduction for each of nine individual test subjects. The individual volunteers were exposed to laser radiation, such as infrared radiation on one leg, and not the other. Both legs were then treated with the massage technique. The protocol was administered for between six and eight weeks. Measurements were taken of the thickness of the fat layers on both legs on a periodic basis throughout the treatment, and noted and recorded. Most of the individuals tested experienced a 5% to 30% reduction in cellulite thickness on the leg with both the laser irradiation treatment and the massage, while there was little to no change in the leg with only the massage therapy. A common side effect was increased urinary frequency. The treatment can cause fluid mobilization from the interstices of the adipocytes or via lipolysis.

An advantage of the present invention is that cellulite levels can be reduced with no "down time" experienced. While other methods of cellulite removal may result in permanent removal of fat, such other methods are more costly, typically require anesthesia, can be painful, and can have further complications including extended "down time".

The teachings of the present invention can be applied in the treatment of other maladies. For example, the method of the present invention can be used for ablation of any unwanted tissue, reduction of edema, treatment of overactive sweat glands, cysts, lipomas, psoriatic tissue, excess lymphatic fluid and tissue, varicose veins, acne, telengiectasias, pain, inflammation, inflammatory products, and other toxins. The method can also be utilized to increase muscle bulk, cause muscle warming, stimulation of bone healing, treatment for "shin splints", tendinitis, tenosynovitis, bone regeneration, and relief of neuralgias, neuromas, and neuropraxias. In each instance, the specific laser wavelengths are adjusted and the aggressiveness and pattern of the massage portion of the treatment varies to correspond to the particular treatment regimen being followed.

Numerous modifications and alternative embodiments of the invention will be apparent to those skilled in the art in view of the foregoing description. Accordingly, this description is to be construed as illustrative only and is for the purpose of teaching those skilled in the art the best mode for carrying out the invention. Details of the structure may vary substantially without departing from the spirit of the invention, and exclusive use of all modifications that come within the scope of the appended claims is reserved. It is intended that the invention be limited only to the extent required by the appended claims and the applicable rules of law.

What is claimed is:

1. A system for treating a condition of a patient, comprising:
   a radiation emitting device for exposing a skin surface of a patient to a radiation wavelength in the visible and infrared wavelength spectrums; and
   a massaging mechanism for massaging the skin surface for a selected time period;
   wherein the exposure of the skin to the radiation wavelength and the massaging of the skin surface treats the condition.

2. The system of claim 1, wherein the radiation-emitting device comprises a laser.

3. The tissue treatment system of claim 1, wherein the massaging mechanism comprises an automated mechanical massaging mechanism.

4. The system of claim 1, wherein the radiation emitting device emits radiation in a concentric combination of infrared radiation and visible radiation.

5. The system of claim 1, wherein the condition comprises having excess cellulite and treatment of the condition comprises a reduction of the excess cellulite.

6. The system of claim 1, wherein the at least one radiation wavelength ranges between 650 nanometers and 1295 nanometers.

7. A method of using a condition treatment system having a radiation emitting device and a massaging mechanism for treating the condition, the method comprising the steps of:
   exposing a skin surface of a patient to radiation emitted from the radiation emitting device at predetermined wavelengths in the visible and infrared spectrums for predetermined periods of time; and
   massaging the exposed skin surface of the patient with the massaging mechanism.

8. The method according to claim 7, further comprising the step of calculating the predetermined wavelengths and the predetermined periods of time based at least partially on a measurement of cellulite in an area of the skin surface being treated.

9. The method according to claim 7, wherein the step of exposing the skin surface comprises applying a laser radiation to the skin surface.

10. The method according to claim 7, wherein the laser radiation applies a concentric combination of infrared and visible laser light to the skin surface.

11. The method according to claim 7, further comprising the step of exposing the skin surface to an application of infrared radiation.

12. The method according to claim 7, wherein the application of infrared radiation occurs in a continuous wave.

13. The method according to claim 11, wherein the application of infrared radiation occurs at predetermined locations on the exposed skin corresponding to lymphatic drainage meridians.

14. The method according to claim 11, wherein the application of infrared radiation heats at least one of deep tissue, tendon, fascia, muscle, and bone within the patient.

15. The method according to claim 7, wherein the step of massaging the exposed skin surface comprises utilizing a mechanical massage mechanism.

16. The method according to claim 7, wherein the step of massaging the exposed skin comprises massaging from points distal from a heart of the patient to points proximal to the heart of the patient to encourage fluid flow toward the heart.

17. The method according to claim 7, wherein the step of massaging the exposed skin comprises massaging in predetermined patterns of motion.

18. The method according to claim 7, wherein the predetermined wavelengths range between about 650 nanometers and 1295 nanometers.

19. The method according to claim 7, wherein the predetermined time periods range between about 5.5 minutes and 12 minutes.

* * * * *